(12) United States Patent
Deffrennes

(10) Patent No.: US 8,166,627 B2
(45) Date of Patent: May 1, 2012

(54) TEMPOROMANDIBULAR PROSTHETIC IMPLANT, AND CORRESPONDING PRODUCTION METHOD

(75) Inventor: Dominique Deffrennes, Paris (FR)

(73) Assignee: OBL, Chatillon (FR)

(*) Notice: Subject to any disclaimer, the term of this patent is extended or adjusted under 35 U.S.C. 154(b) by 477 days.

(21) Appl. No.: 12/293,058

(22) PCT Filed: Mar. 8, 2007

(86) PCT No.: PCT/FR2007/000414
§ 371 (c)(1),
(2), (4) Date: Dec. 17, 2008

(87) PCT Pub. No.: WO2007/104850
PCT Pub. Date: Sep. 20, 2007

(65) Prior Publication Data
US 2009/0222102 A1  Sep. 3, 2009

(30) Foreign Application Priority Data
Mar. 15, 2006  (FR) ................................ 06 02268

(51) Int. Cl.
*B23P 13/04* (2006.01)
*A61F 2/02* (2006.01)
(52) U.S. Cl. .................... 29/558; 29/557; 623/17.17
(58) Field of Classification Search ............... 29/557, 29/558; 623/17.17
See application file for complete search history.

(56) References Cited

U.S. PATENT DOCUMENTS

| | | | | |
|---|---|---|---|---|
| 2,579,643 A * | 12/1951 | Baak | ............... | 60/611 |
| 3,178,728 A * | 4/1965 | Christensen | ............... | 623/17.17 |
| 4,502,161 A * | 3/1985 | Wall | ............... | 623/14.12 |
| 4,693,722 A * | 9/1987 | Wall | ............... | 623/17.17 |
| 4,778,472 A * | 10/1988 | Homsy et al. | ............... | 623/17.17 |
| 4,917,701 A * | 4/1990 | Morgan | ............... | 623/17.17 |
| 4,936,852 A * | 6/1990 | Kent et al. | ............... | 623/17.17 |
| 5,405,393 A * | 4/1995 | Falkenstrom | ............... | 623/17.17 |
| 5,445,650 A * | 8/1995 | Nealis | ............... | 623/17.17 |
| 5,489,305 A * | 2/1996 | Morgan | ............... | 623/17.17 |
| 5,549,680 A * | 8/1996 | Gordon | ............... | 623/17.17 |
| 6,132,466 A * | 10/2000 | Hoffman et al. | ............... | 623/17.17 |

(Continued)

FOREIGN PATENT DOCUMENTS

DE  3605776 A1  3/1987

(Continued)

OTHER PUBLICATIONS

English language abstract of FR 2,558,721, Aug. 2, 1985.

(Continued)

*Primary Examiner* — David Bryant
*Assistant Examiner* — Jacob Cigna
(74) *Attorney, Agent, or Firm* — Pearne & Gordon LLP

(57) ABSTRACT

The prosthetic temporomandibular implant (10) comprises a concave surface (16) and a convex surface (17) designed to cooperate, respectively, with the natural outer surface (9) of the condyle (5) and the natural inner surface (7) of the fossa (8) of a damaged joint (2) of a human mandible (1). It is made of a rigid biocompatible material such as ceramic, stainless steel or an aluminum/zirconium alloy. The implant is designed based on an image of the joint (2) generated by a medical imaging system and incorporating an image of a healthy joint (3); these three-dimensional images are processed by a CAD (segmentation, vectorization) system to obtain a vector representation of the implant (10) and a data file capable of controlling a digital milling machine. The invention is applicable to the restoration of a damaged TMJ (2).

12 Claims, 2 Drawing Sheets

U.S. PATENT DOCUMENTS

| | | | |
|---|---|---|---|
| 6,702,855 B1 * | 3/2004 | Steinemann et al. | 623/23.53 |
| 6,772,026 B2 * | 8/2004 | Bradbury et al. | 700/98 |
| 2008/0261168 A1 * | 10/2008 | Gutman et al. | 433/69 |

FOREIGN PATENT DOCUMENTS

| | | | |
|---|---|---|---|
| EP | 0337749 A1 | | 10/1989 |
| FR | 2558721 A1 | | 2/1985 |
| RU | 2146507 C1 | * | 3/2000 |
| WO | 03/030787 A1 | | 4/2003 |
| WO | 2004/080340 A2 | | 9/2004 |

OTHER PUBLICATIONS

English language abstract of DE 3,605,776, Oct. 6, 1988.

* cited by examiner

TEMPOROMANDIBULAR PROSTHETIC IMPLANT, AND CORRESPONDING PRODUCTION METHOD

TECHNICAL FIELD OF THE INVENTION

The present invention relates to a prosthetic implant for reconstructing a temporomandibular joint that has become non-functional, and a method for producing this implant.

TECHNOLOGICAL BACKGROUND OF THE INVENTION

A comprehensive analysis of the specific characteristics of a temporomandibular joint, also known as a temporomaxillary joint, as compared to the other diarthroses of the human body, is made in French patent application FR 2,558,721 in the name of the company Landos—Application Orthopédique Francaise, published on Aug. 2, 1985, in the preamble to the description of a prosthesis for a joint of this type.

The temporomandibular joint (abbreviated TMJ) is delimited by a cranial articular surface underlying the temporal bone and by an articular surface overlying the mandible. The glenoid fossa of the TMJ is pellucid since the bony layer that isolates the fossa from the overlying cranial mass is between several tenths of a millimeter and a maximum of two millimeters thick. The mandibular articular surface is constituted by the condyle, which surmounts the ascending branch of the mandible.

Between the temporal and mandibular articular surfaces is a fibrocartilaginous meniscus that covers the mandibular condyle and is continuous with the outer pterygoid muscle so that the meniscus is partly responsible for the movements that open the mouth.

The dynamics of TMJs are very distinctive, and unlike "closed" joints like those of the elbow or the knee, the temporomandibular joint is an "open" joint. It is a joint that is "suspended" from the skull, both by its own means and by the elevator muscles.

Taking into account these anatomical constraints, the above-mentioned patent application proposes a TMJ prosthesis comprising a self-tapping threaded screw surmounted by a ball-shaped head that cooperates with the spherical cavity of a socket. The threaded screw is designed to be screwed into the ascending branch of the mandible, and the socket is placed in the glenoid fossa of the joint.

This prosthesis allows the complex movements of the natural joint, but its ball-and-socket-based structure is reminiscent of the techniques used for the joints of the long bones.

Thus, it does not seem particularly suited to a TMJ. Moreover, its implantation is, quite clearly, particularly invasive.

In order to minimize the surgical procedure as much as possible, and particularly to avoid ablating a usable part of the condyle, European patent application EP 0,337,749 in the name of the company Vitek, published on Oct. 18, 1989, teaches the use of a "mini" temporomandibular condyle prosthesis that cooperates with an adapted glenoid fossa prosthesis.

The condyle prosthesis described is right-angle shaped, one branch being laterally attached to the natural condylar neck. The other branch has a convex surface that defines the articular surface of the artificial condyle.

The implantation of this prosthesis does not require an incision below the angle of the jaw, but makes it necessary to form a shoulder capable of receiving the upper end of the natural condyle.

According to another method for reconstructing a TMJ, German patent application DE 3,605,776 in the name of D. Kubein-Meesenburg, published on Sep. 3, 1987, proposes a meniscal endoprosthesis.

What characterizes this prosthesis is that it is made of flexible plastic material and can be adapted to the shape of the TMJ.

In order to help maintain it in position, this prosthesis is in the shape of a disk wherein the top surface in contact with the fossa has a radius of curvature larger than the radius of curvature of the bottom surface in contact with the condyle.

However, the practitioner knows that it is impossible to attach this type of prosthesis to either the muscles or the ligaments, and thus, in addition to the fact that the implantation of a prosthesis made of plastic material is not recommended for more than three months, the durability of such a solution is doubtful, since the essential characteristic of the temporomandibular joint is that it is an open joint.

The upshot of the prior art described above is that there are many known types of TMJ endoprostheses, but that to date, there is no existing model that meets the precise needs of specialists in maxillofacial surgery, i.e. a prosthetic implant having a long life that can be implanted in a very non-invasive way.

GENERAL DESCRIPTION OF THE INVENTION

The present invention concerns a prosthetic temporomandibular implant of the type comprising a concave surface designed to cooperate, at least in part, with a first natural outer surface of the condyle of a first joint of a mandible, and a convex surface designed to cooperate, at least in part, with a first natural inner surface of the fossa of this first joint.

Unlike the known prostheses of this type made of flexible material, the prosthetic implant according to the invention is noteworthy in that it is composed of rigid material.

According to an additional feature, the concave surface of this implant is advantageously porous.

Preferably, the material of which the implant is formed is ceramic.

Alternately, this material is a metal alloy, preferably stainless steel or an aluminum/zirconium alloy.

Another subject of the present invention is a method for producing the prosthetic temporomandibular implant briefly described above.

Unlike certain prostheses known in the prior art, made of flexible material and molded in vivo to the shape of the joint, the invention proposes forming the implant ex vivo based on at least one first image of the first inner and outer surfaces of the first joint.

In the production method according to the invention, the implant is advantageously also formed based on at least one second image of a second natural outer surface of the condylar neck and of the second natural inner surface of the glenoid fossa of the second joint of the mandible.

The at least first and at least second images are preferably three-dimensional representations generated by a medical imaging system such as a tomograph.

The advantage of the invention is that the implant is formed based on a data file representing the shape of this implant.

In this case, these data are advantageously generated using a computer-aided design system, by comparing the at least first and at least second images in order to restore the bilateral symmetry of the first and second joints.

Alternately, or simultaneously, the production method according to the invention is noteworthy in that at least the first image is that of a first, damaged joint and the second image is that of a second, healthy joint. The data are thus a vector representation of the implant generated by simulation, using a computer-aided design system to partially fill in the virtual interarticular space corresponding to the gap between the first outer surface and the virtual symmetrical surface of the second outer surface relative to the overall plane of symmetry of the mandible, and to the gap between this virtual surface and the first inner surface.

According to the method of the invention, the implant is preferably given its final shape by milling the base material using a digitally controlled milling machine, based on the data file generated in the previous steps.

In the method according to the invention, the concave surface of the prosthetic implant advantageously has a shape that is exactly complementary to the shape of the adjacent portion of the first outer surface.

Another advantage of the invention is that the concave surface of the implant is subjected to chemical etching in order to facilitate osteointegration.

These few essential specifications make the advantages of this device over the prior art clear to a person skilled in the art.

The detailed specifications of the invention are given in the description below in connection with the attached drawings. It should be noted that the drawings serve merely to illustrate the text of the description and do not constitute any sort of limitation of the scope of the invention.

DESCRIPTION OF A PREFERRED EMBODIMENT OF THE INVENTION

Figure 1:
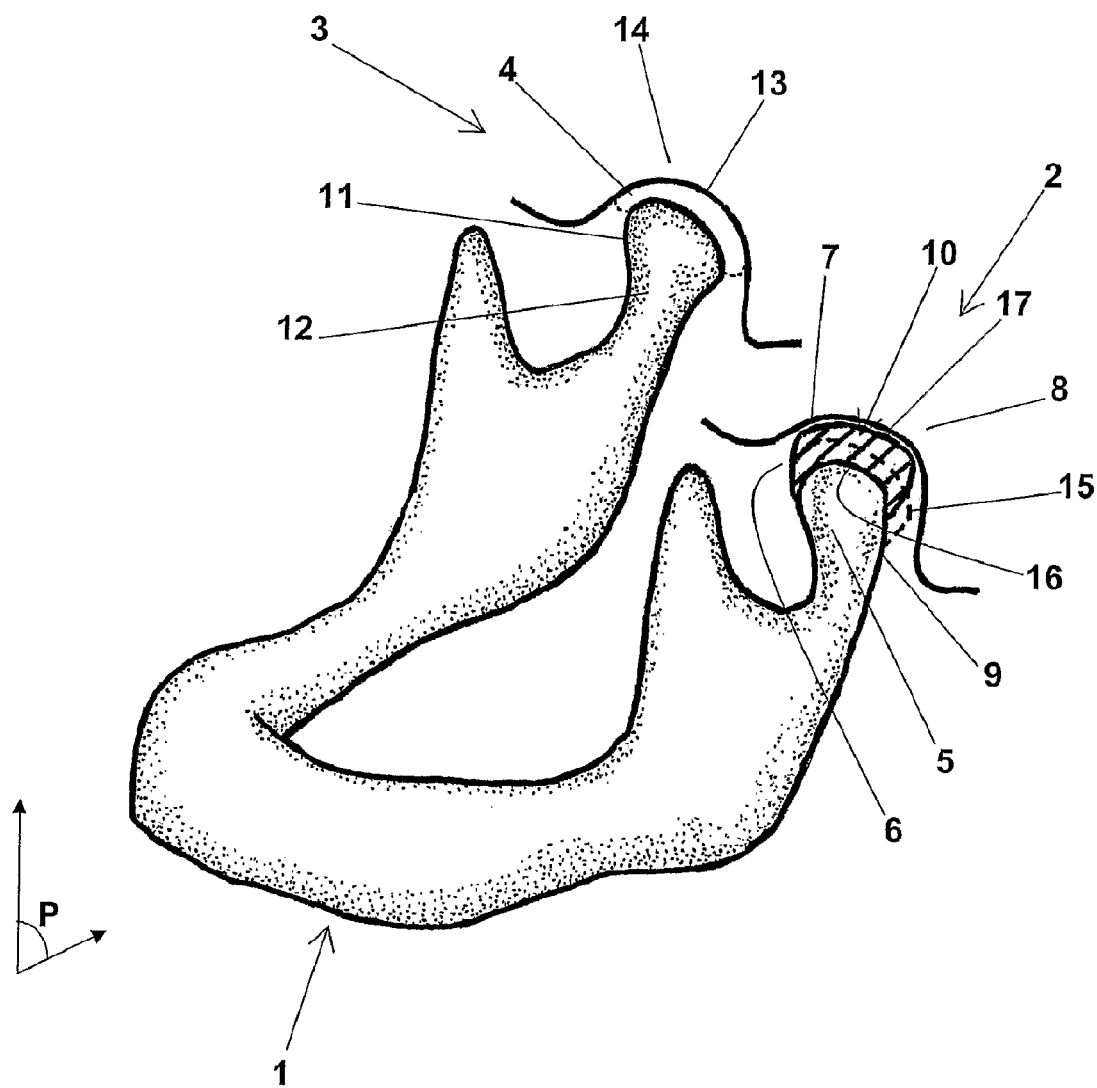
FIG. 1 schematically illustrates an implant simulation corresponding to the method for producing the prosthetic temporomandibular implant according to the invention.
Figure 2:
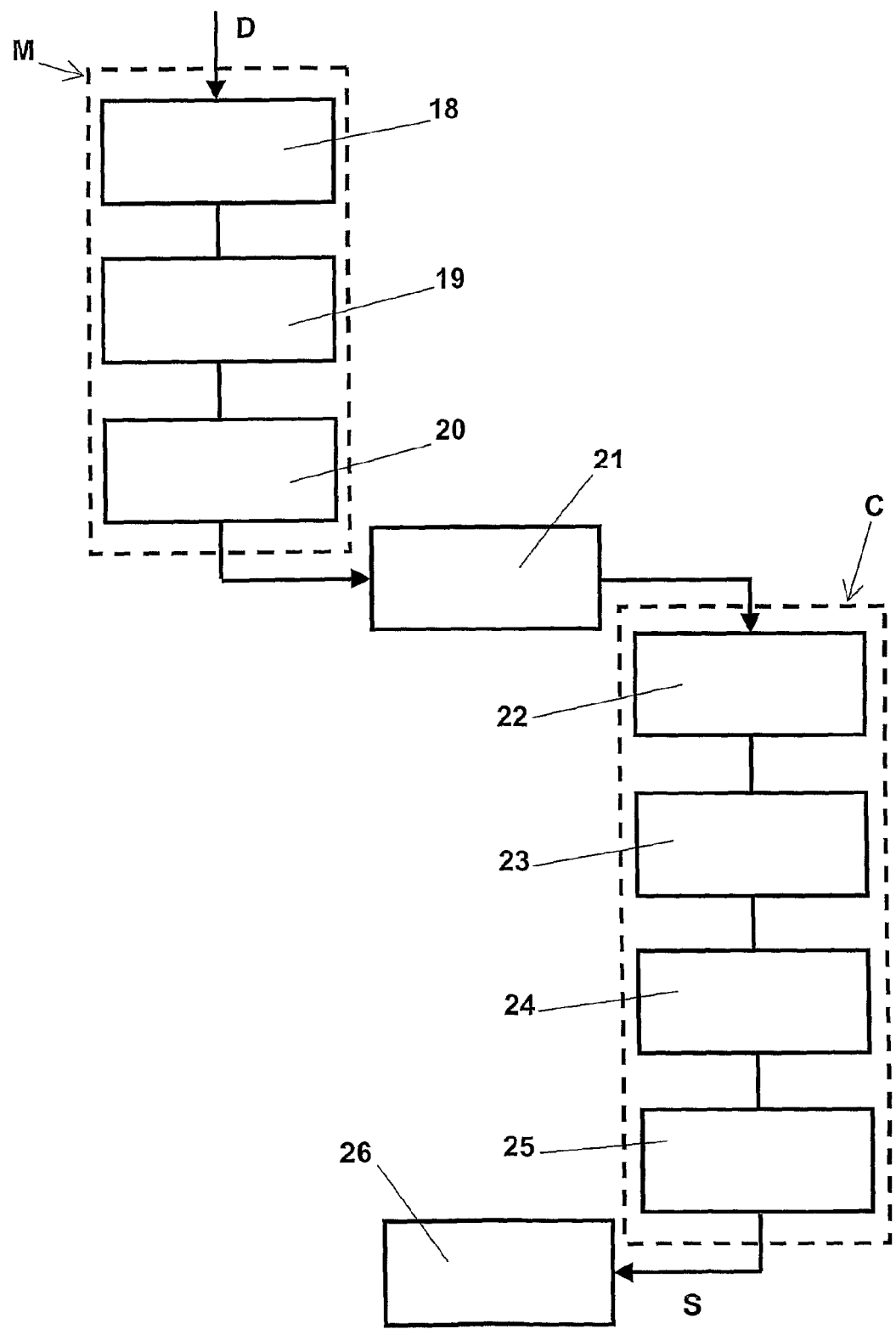
FIG. 2 schematically illustrates the various steps in the method for producing the prosthetic temporomandibular implant according to the invention.

The references to FIGS. 1 and 2 will serve to explain in detail the features of the prosthetic temporomandibular implant 1 according to the invention, and those of the corresponding production method.

FIG. 1 shows a simplified transcription of a three-dimensional representation of a human mandible 1 like that generated by a piece of software for processing data produced by a medical imaging device.

This device is a system capable of providing a highly precise image of the part of the human body in question, for example a tomograph or a magnetic resonance imaging (MRI) device.

The format of the data output from this system is often of a so-called "proprietary" nature, but more and more frequently tends to adhere to the DICOM ("Digital Imaging and Communication in Medicine") standard.

The MIMICS® software from the company Materialise, for example, is capable of processing the data resulting from a cranial examination by any scanner using the DICOM standard, and of producing an image similar to FIG. 1.

In the normal state, a patient's mandible 1 and temporomandibular joints 2, 3 have a substantial bilateral symmetry, i.e. a symmetry relative to an antero-posterior median plane P.

When a first joint 2 is damaged, the meniscus 4 present in a normal joint 3 has often disappeared and the condyle 5 has been abraded.

For this reason, the real image shows a dissymmetry of the TMJs 2, 3, which the computer reconstruction makes it possible to correct.

FIG. 1 clearly shows, at the level of the first joint 2, a virtual interarticular space 6 between the first inner surface 7 of the fossa 8 and the first outer surface 9 of the condyle 5 resulting from this simulation.

In order to restore the functionality of this damaged joint 2, the invention proposes covering the condyle 5 with a prosthetic temporomandibular implant 10 made of rigid material.

This implant 10 (shown in cutaway in FIG. 1) partly fills in the virtual interarticular space 6 by replacing both the missing part of the condyle and the absent meniscus.

Observing the second, healthy joint 3 makes it possible to determine the optimal shape for the implant 10.

The second outer surface 11 of the condylar neck 12 of this joint 3 opposite the second inner surface 13 of the glenoid fossa 14 essentially determines, based on a symmetry P, a virtual surface 15 that makes it possible to estimate the height to give the implant 10.

The concave surface 16 of the implant 10, which cooperates with the first outer surface 9, is porous so as to facilitate osteointegration.

On the other hand, the convex surface 17 of the implant 10 is perfectly smooth so as to minimize the friction on the first inner surface 7 of the fossa 8.

In this context, materials such as ceramics, or metal alloys like stainless steel or an aluminum/zirconium alloy, have advantageous mechanical properties while being biocompatible.

The steps of the method for producing this prosthetic temporomandibular implant 10 are schematically represented in FIG. 2.

In a first step 18, the patient data D generated by a medical imaging device are input into a computer system in order to be processed by implant simulation software M such as the MIMICS® software.

A processing performed during a second step 19, under the control of an operator, makes it possible to isolate the 3D representations of the patient's mandible 1 and superior maxilla, and particularly the condyles 5, 12 and the glenoid fossae 8, 14.

At this stage 18, 19 of the simulation, the 3D representations are three-dimensional images constituted by "scatters" of points (which are more or less dense, depending on the resolution of the system).

This type of image is not adapted to manipulation by conventional computer-aided design (CAD) or computer-aided manufacturing (CAM) systems, which are based on the generation of vector images.

Thus, during a third step 20, the images output by the segmentation step 19 are converted to the STL format by the simulation software M (MIMICS®, for example).

The STL format is a format originally developed for controlling stereolithography machines (STL is the acronym for "StereoLithographic"). It consists of approximately representing the three-dimensional surface of an object with a mesh of contiguous triangles, i.e. with the coordinates of all of the vertices of these triangles.

This format is the native format for the export of data from the MIMICS® software, designed mainly for producing "imprints" from scanners.

It is a "vector" format suitable for use by a CAD or CAM system. However, the STL format represents surfaces and not solids, leading to problems when there is a need to produce cross-sections.

Thus, during a fourth step 21, the STL surface file is converted into a vector-based solid file in the STEP format or in a format specific to the CATIA® Version 5 software developed by the company Dassault Systémes.

The STEP ("Standard for the Exchange of Product Model Data") and CATIA® formats are equivalent in that CATIA (the acronym for "Computer-Aided Three-Dimensional Interactive Application") software is preferably used in the operational sequence C and CATIA® Version 5 has a STEP import module.

During a fifth step 22, CAD software is used to create a cube on the scale of the desired implant 10, i.e. an implant corresponding to the virtual interarticular space 6 represented in FIG. 1.

During a sixth step 23, Boolean operations consisting of subtracting the condyle 5 and the maxilla 8 from the cube are performed so as to obtain, respectively, the concave surface 16 and the convex surface 17 of the implant 10.

The result of these operations is obtained in a file format that is better adapted to CAM systems during a seventh step 24, preferably in the IGES (Initial Graphics Exchange Specification) format.

In an eighth step 25, an erosion operation is performed to reduce the upper surface of the anatomical piece 10 by a few millimeters, in accordance with the condylar neck 12 of the opposite joint 3.

The output from the CAD system C is a data file S for controlling a digitally controlled milling machine, and for automatically producing the implant 10 during a final step 26.

Preferably, the production method according to the invention also includes an additional step during which the concave surface 16 of the implant 10 is chemically etched to make it porous.

At the end of the third step 20, the STL file is advantageously used to produce, using stereolithography, imprints of the patient's mandible 1 and TMJs 2, 3, in order to verify the adaptation of the implant 10 produced in the final step 26.

The precision of the production chain D, M, 21, C, 26 makes it possible to obtain a prosthetic implant 10 whose concave surface 16 is exactly complementary to the part of the condyle 5 that it covers.

For this reason, the stability of the prosthesis is ensured without the need for a preparation of the condyle 5, and particularly without the formation of facets, as was the case in the prior art.

The insertion of the implant according to the invention thus requires a far less invasive surgical procedure than used to be required.

This surgical method, while nonpatentable per se, is made possible by the production method described above, which in the case of the temporomandibular joint 2,3 practically solves the difficult technical problem of using data from a scanner, i.e. 3D voxel representations, in a conventional CAD system using vector representations.

It is understood that the invention is not limited to the above technical specifications, which are given merely as examples; on the contrary, it encompasses all of the possible variants of embodiment.

In particular, the file formats are indicated only as examples. They correspond to the dedicated software used, whose names are nonlimiting and are given merely to illustrate a choice that a person skilled in the art could easily expand.

The use of any other data file format using voxel or vector representation, depending on the circumstances, to produce the prosthetic temporomandibular implant according to the invention would not exceed the scope of the present invention as long as the features of the production method remain within the context of the following claims.

The invention claimed is:

1. Method (M, 21, C, 26) for producing a prosthetic temporomandibular implant (10), of the type comprising a concave surface (16) designed to cooperate, at least in part, with a first natural outer surface (9) of the condyle (5) of a first joint (2) of a mandible (1), and a convex surface (17) designed to cooperate, at least in part, with a first natural inner surface (7) of the fossa (8) of said first joint (2), characterized in that said implant (10) is composed of rigid material, the method comprising the steps of:

generating at least one first image of said first natural inner (7) and natural outer (9) surfaces of said first joint (2);

generating a data file (S), based upon said at least one first image, that is a vector representation of said implant (10) by simulation, using a computer-aided design system (M, C) to partially fill in a virtual interarticular space (6) corresponding to a gap between said first natural inner (7) and natural outer (9) surfaces; and manufacturing said implant (10) using a digitally controlled machine, based on said data file (S).

2. Method (M, 21, C, 26) for producing a prosthetic temporomandibular implant (10) according to claim 1, characterized in that said concave surface (16) has a shape that is exactly complementary to the shape of the adjacent portion of said first outer surface (9).

3. Method (M, 21, C, 26) for producing a prosthetic temporomandibular implant (10) according to claim 1, characterized in that said concave surface (16) is subjected to chemical etching in order to facilitate osteointegration.

4. Method (M, 21, C, 26) for producing a prosthetic temporomandibular implant (10) according to claim 1, characterized in that said concave surface (16) is porous.

5. Method (M, 21, C, 26) for producing a prosthetic temporomandibular implant (10) according to claim 1, characterized in that said material is ceramic.

6. Method (M, 21, C, 26) for producing a prosthetic temporomandibular implant (10) according to claim 1, characterized in that said material is a metal alloy, preferably stainless steel or an aluminum/zirconium alloy.

7. Method (M, 21, C, 26) for producing a prosthetic temporomandibular implant (10) according to claim 1, characterized in that said implant (10) is also formed based on at least one second image of a second natural outer surface (11) of the condylar neck (12) and of the second natural inner surface (13) of the glenoid fossa (14) of the second joint (3) of said mandible (1).

8. Method (M, 21, C, 26) for producing a prosthetic temporomandibular implant (10) according to the above claim 7, characterized in that said at least first and at least second images are three-dimensional representations (D) generated by a medical imaging system, preferably a tomograph.

9. Method (M, 21, C, 26) for producing a prosthetic temporomandibular implant (10) according to claim 7, characterized in that said implant (10) is formed based on a data file (S) including both of said first and second images representing the shape of said implant (10).

10. Method (M, 21, C, 26) for producing a prosthetic temporomandibular implant (10) according to claim 9, characterized in that said data (8) are generated using a computer-aided design system (M, C) by comparing said at least first and at least second images in order to restore the bilateral symmetry of said first (2) and second (3) joints.

11. Method (M, 21, C, 26) for producing a prosthetic temporomandibular implant (10) according to claim 9, characterized in that said at least first image is that of a first, damaged joint (2) and said second image is that of a second, healthy joint (3), and in that said data (8) file is a vector representation of said implant (10) generated by simulation, using a computer-aided design system (M, C) to partially fill in the virtual interarticular space (6) corresponding to a gap between said first natural outer surface (9) and a virtual symmetrical surface (15) of said second natural outer surface (11) relative to an overall plane of symmetry (P) of said mandible (1), and to a gap between said virtual surface (15) and said first natural inner surface (7).

12. Method (M, 21, C, 26) for producing a prosthetic temporomandibular implant (10) according to claim 9, characterized in that said implant (10) is shaped by milling (26) said material using a digitally controlled milling machine, based on the data file (S).

* * * * *